US012105081B2

(12) United States Patent
Kimmerling et al.

(10) Patent No.: US 12,105,081 B2
(45) Date of Patent: Oct. 1, 2024

(54) TREATMENT RESPONSE ASSESSMENT USING NORMALIZED SINGLE CELL MEASUREMENTS

(71) Applicant: Travera, Inc., Medford, MA (US)

(72) Inventors: Robert Kimmerling, Cambridge, MA (US); Selim Olcum, Cambridge, MA (US); Mark Stevens, Cambridge, MA (US)

(73) Assignee: Travera, Inc., Medford, MA (US)

( * ) Notice: Subject to any disclaimer, the term of this patent is extended or adjusted under 35 U.S.C. 154(b) by 0 days.

(21) Appl. No.: 17/729,644

(22) Filed: Apr. 26, 2022

(65) Prior Publication Data

US 2023/0119020 A1    Apr. 20, 2023

Related U.S. Application Data

(60) Provisional application No. 63/278,420, filed on Nov. 11, 2021, provisional application No. 63/257,906, filed on Oct. 20, 2021.

(51) Int. Cl.
*G01N 33/50* (2006.01)
*B01L 3/00* (2006.01)

(52) U.S. Cl.
CPC .... *G01N 33/5011* (2013.01); *B01L 3/502761* (2013.01); *G01N 33/5032* (2013.01); *B01L 2200/0652* (2013.01)

(58) Field of Classification Search
None
See application file for complete search history.

(56) References Cited

U.S. PATENT DOCUMENTS

| | | | |
|---|---|---|---|
| 8,418,535 | B2 | 4/2013 | Manalis et al. |
| 9,132,294 | B2 | 9/2015 | Zheng et al. |
| 2015/0198584 | A1 | 7/2015 | Rajwa et al. |
| 2021/0128557 | A1 | 5/2021 | Shalek et al. |

FOREIGN PATENT DOCUMENTS

| | | | | |
|---|---|---|---|---|
| WO | WO-2018236708 | A1 | * 12/2018 | ........ B01L 3/502715 |
| WO | WO-2020102595 | A1 | * 5/2020 | ......... G01N 33/5017 |

OTHER PUBLICATIONS

Stockslager, Max A., et al. "Functional drug susceptibility testing based on biophysical measurements predicts patient outcome in glioblastoma patient-derived neurosphere models." bioRxiv (2020). Published online Aug. 6, 2020 at: https://www.biorxiv.org/content/10.1101/2020.08.05.238154v1.full (Year: 2020).*
Curtis, Michael J., et al. "Experimental design and analysis and their reporting II: Updated and simplified guidance for authors and peer reviewers." British journal of pharmacology 175.7 (2018): 987-993. (Year: 2018).*
Bendall, Sean C., et al. "Single-cell mass cytometry of differential immune and drug responses across a human hematopoietic continuum." Science 332.6030 (2011): 687-696 (with supplementary material attached). (Year: 2011).*
Burg, 2007, Weighing of biomolecules, single cells and single nanoparticles in fluid, Nature 446:1066-1069.
Cermak, 2016, High-throughput measurement of single-cell growth rates using serial microfluidic mass sensor arrays, Nat Biotechnol 34(10):1052-1059.
Greenbaum, 2012, Imaging without lenses: achievements and remaining challenges if wide-field on-chip microscopy, Nat Methods 9(9):889-895.
Lee, 2011, Suspended microchannel resonators with piezoresistive sensors, Lap Chip 11:645, 7 pages.
Bendall, Sean C, et al., "Single-Cell Mass Cytometry of Differential Immune and Drug Responses Across a Human Hematopoietic Continuum", Science 332.6030 (2011) 687-696.
Curtis, Michael J, et al., "Experimental design and analysis and their reporting Il: updated and simplified guidance for authors and peer reviewers", British Journal of Pharmacology 175.7 (2018): 987-993.
Stockslager, Max A, et al., "Functional drug susceptibility testing based on biophysical measurements predicts patient outcome in glioblastoma patient-derived neurosphere models", bioRxiv (Pub. Online Aug. 6, 2020).
"International Search Report issued in International Application No. PCT/US2022/047231, Date of Mailing: Jan. 11, 2023, 2 pages".
"Final Office Action issued in U.S. Appl. No. 17/729,644, Date of Mailing: Dec. 7, 2023, 14 pages."
"Non-Final Office Action issued in U.S. Appl. No. 17/729,644, Date of Mailing: Aug. 16, 2023, 16 pages."
"Final Office Action issued in U.S. Appl. No. 17/729,644, Date of Mailing: Apr. 26, 2023, 14 pages."
"Non-Final Office Action issued in U.S. Appl. No. 17/729,644, Date of Mailing: Jan. 3, 2023, 12 pages."

* cited by examiner

*Primary Examiner* — Robert J Yamasaki
(74) *Attorney, Agent, or Firm* — Withers Bergman LLP; Thomas C. Meyers (57) ABSTRACT

The present invention includes methods and systems for assessing a cellular response to a treatment modality, such as potential drug candidate, by comparing normalized single-cell measurements of cellular properties without the need of a calibration step.

20 Claims, 5 Drawing Sheets

TREATMENT RESPONSE ASSESSMENT USING NORMALIZED SINGLE CELL MEASUREMENTS

TECHNICAL FIELD

This invention relates generally to methods of measuring a functional biomarker without calibrating the measurement system.

BACKGROUND

Precision medicine is an approach to medicine that involves the customization of healthcare for individual patients. Clinical tests, decisions, and treatments are tailored to the individual patient. In this approach, diagnostic testing is generally used to select therapies based on an individual patient's genetic content or other molecular or cellular analysis performed on specimens collected from the patient. Alternatively functional biomarkers that measure and predicts the outcome of treatments for a patient are used for precision medicine and determining personalized therapies for individual patients.

Precision medicine refers to the tailoring of medical treatment to the individual characteristics of each patient and also could include the ability to classify individuals into subpopulations based on susceptibility to a particular disease or treatment. Precision medicine often involves genomic analysis of a patient and treatment selection based on genetic markers. Therapeutic intervention is provided to patients who will benefit, sparing expense and side effects to those patients unlikely to benefit. The treatment response for the patient is then tracked, often using surrogate measures such as imaging tumor load, or measuring tumor markers in peripheral blood. Treatment is finely adapted to the tracked response.

Change of cell mass in specimens collected from patients in response to a treatment have been used as an indicator of treatment response. However, existing modalities that measure changes in cell mass require well controlled instruments and laborious calibration steps, are prone to phenotypic drift of the cells ex vivo, and often require long assay times.

SUMMARY

The present invention includes methods and systems for assessing a cellular response to a treatment, such as a potential drug candidate. The invention is useful with any single cell measurement modality measuring a cellular property, such as mass, volume, diameter, impedance, capacitance, resistance, optical properties, fluorescence intensity, density, stiffness, surface friction, deformation, cell-cycle state, viability, differentiation state, activation state, fluorescent properties and others, which is or are altered by a treatment or stimulus applied to the cell. The treatment may be any perturbation of the cell and includes a therapeutic, an allergen, a toxin, an environmental stimulus, an electrical impulse, a change in pressure, salinity, water content or other cellular perturbations. As provided in detail below, the exact nature of the perturbation is immaterial to the operation of the invention. Moreover, the treatment or stimulus can be introduced in vivo in an ex vivo sample or to a single cell or population of cells in isolation.

An exemplary method comprises exposing live cells in a sample to a treatment or stimulus. The treatment, in addition to those described above, may include, for example, a therapeutic (or potential therapeutic) agent (e.g., small molecules, mRNA, anti-sense oligonucleotides), radiation, immune cell activators, antibodies, cells, viruses, and the like.

The invention provides methods for assessing cellular response to a treatment opr stimulus, which include measuring a portion of treated cells individually and a portion of untreated cells individually from the same sample in a device that includes a measurement sensor to measure the cellular property. Comparing those populations of single cell measurements reveals a relative response signal indicative of a cellular response to the treatment or stimulus. As applied to living cells, the ability of the presently-disclosed systems and methods to measure a rapid response to a treatment or stimulus leads to results being obtained prior to any significant change in cellular property (e.g., loss of mass, reduction in size, loss of image contrast etc.) due to natural, biological time variation or other effects.

Certain methods of the invention include sequentially measuring untreated and treated cells using a measurement device. In certain preferred methods, the measuring steps include sequentially measuring cells of a first untreated portion of cells from the sample, then the treated portion of cells, and finally a second untreated portion of cells from the sample.

In certain methods, the comparing step may include comparing the first untreated portion of cells and the second untreated portion of cells. Comparing the untreated portions may provide a maximum baseline difference of the cellular property over the time of measurements. This maximum baseline difference represents the natural time variability of the cells, i.e., that is independent of the treatment modality. The comparing step may further include determining the relative difference between the treated cells and of the first portion of untreated cells versus the maximum baseline difference of the measured cellular property. This provides the net response signal of the cells to the treatment or stimulus and accounts for any natural time variability of the cells.

In certain aspects, the treatment includes contacting the portion of cells from the sample with a potential therapeutic. Methods of the invention are then used to assess a therapeutic effect of the treatment based on a change in the distribution of the cellular property of the first portion of untreated cells compared to the treated portion of the cells.

In certain embodiments, a response signal to a treatment is calculated using the statistical difference between the distributions of the cellular property of the treated cells versus untreated cells that are measured at the same sensor.

In certain embodiments, the statistical difference is quantified as a statistical distance between measurements of treated versus untreated cells such as Hellinger distance, Wasserstein (earth mover's) distance, Kullback-Leibler (KL) divergence, total variation distance, Bhattacharyya distance, Kolmogorov-Smirnov (KS) distance, Mahalanobis distance, and other related measures. In such embodiments, the magnitude of the calculated distance may provide a measure of the treatment response of the cells.

In certain embodiments, the statistical distance is calculated using measurements of the untreated and treated cells normalized to a property selected from a population mean, median, distribution mode, etc. Such normalization provides a unitless measurement of the cellular property. In such embodiments, the measured statistical distance is independent of the sensor calibration. In such embodiments, the magnitude of the signal created by the measurement sensor is used to compare treated and untreated cells without the need for calibrating the sensor and converting the unit of the signal magnitude to that of the cellular property.

In certain aspects, the first untreated portion of cells, the treated portion of cells, and the second untreated portion of cells are introduced into the device separately and sequentially.

In other methods and systems, the mass of each cell is measured as the cellular property by a mass sensor. Measuring changes in cellular mass reveals, for example, if cells are growing, stationary, or undergoing atrophy or a mass reduction. Thus, a change in the mass of a cell exposed to a treatment, e.g., a potential therapeutic, is indicative of a cellular response to the treatment. In such systems the mass sensor may be a Suspended Microchannel Resonator (SMR).

An SMR weighs single mammalian cells with a resolution of about 0.05 pg (0.1% of a cell's buoyant mass) or better. The present invention uses this high resolution to obtain accurate mass distributions for living cells that are introduced into the device and flow through a microchannel of the SMR. Importantly, the masses of treated cells and the masses untreated cells are obtained using the same SMR sensor. Using the same sensor for measuring both the test and the control cells, the present invention enables normalized cellular treatment response signals without the need to calibrate the SMR.

Systems and methods of the invention are amenable to high throughput. In certain aspects, methods and systems of the invention measure the mass of about 500 or more individual cells per minute. This is a dramatic improvement over existing methods for measuring, for example, the precise mass accumulation rate (MAR), which often requires ten or more measurements and two hours for ~200 cells or less to be measured.

Methods of the invention may include labeling the treated and/or untreated cells with a detectable label, such as an optically detectable label. The SMR device may have a sensor operating over a sensor region that detects the label to distinguish, for example, treated cells from untreated cells or cancer cells from healthy cells or cancer cells from tissue debris or dead cells.

In certain aspects, the treated and untreated cells are introduced into the device together, and the treated cells are labeled. The device may include a sample channel, a secondary channel in which the SMR sensor is disposed. The device detects the label using an additional sensor in series with the SMR and a classifier identifies a cell as a treated or untreated cell using the label.

Methods of the invention are also useful for comparing mass of single cells in treated and untreated populations to determine the therapeutic effect of a treatment using an SMR sensor.

A common feature of all methods of the invention is the lack of a calibration step. Rather, method disclosed herein rely on normalized measurement comparisons. This advantage enables accurate comparisons across samples as well as from laboratory to laboratory.

DETAILED DESCRIPTION

The present invention includes methods and systems for assessing a cellular response to a treatment or stimulus, such as a cancer drug, or a prospective therapeutic. Testing putative treatments on tumor specimens acquired from patients is useful for guiding individualized treatment strategies.

In methods and systems of the invention, a single sensor specifically designed to measure a property of cells, such as mass, volume, diameter, impedance, capacitance, resistance, optical properties, fluorescence intensity, density, stiffness, surface friction, deformation, cell-cycle state, viability, differentiation state, activation state, fluorescent properties and other physical and chemical properties of the cell, that is or are expected to change in response to a treatment. It was previously demonstrated that cellular parameters may be altered in response to external cues, such as drugs introduced in vitro. Therefore, identifying and quantifying changes in cellular parameters in response to various treatments is useful to identify the best therapeutic options for individual patients.

Figure 1:
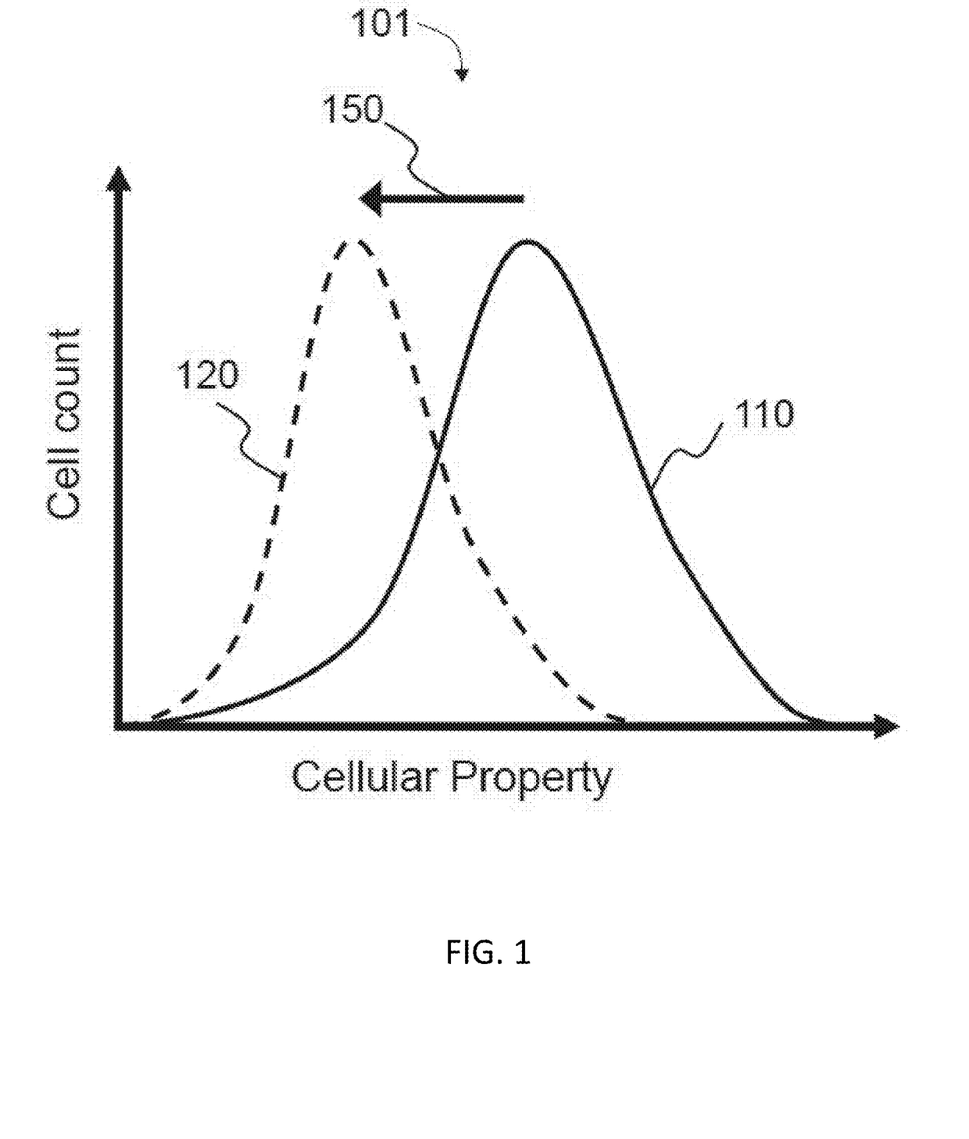
FIG. 1 shows a schematic of an SMR device.

Referring to FIG. 1, a feature of a sensor for use in the invention is its capability of precisely measuring the cellular property of interest at a single cell level, and doing so at high throughput so that a population of single cells can be measured sequentially revealing a distribution of the cellular property 110 in the population of interest. The invention allows for the comparison of population measurements of treated 110 and untreated 120 single cells quickly and precisely to reveal the treatment response on the cells.

For example, immediately after a biopsy, the tumor cells extracted from a patient start to lose their viability in the ex vivo and naturally start to change. The rate of biological time variability depends on the conditions in which the cells are kept, as well as on tumor type and it varies across patients. Given enough time, cellular time variability manifests itself as changes in cellular properties 150, such as mass, volume, diameter, impedance, capacitance, resistance, optical properties, fluorescence intensity, density, stiffness, surface friction, deformation, cell-cycle state, viability, differentiation state, activation state, fluorescent properties etc. Therefore, monitoring of baseline variability due to time of the cellular property of interest is critical to accurately extract response of the cells to drug alone.

Conventionally, monitoring single cells for an extended period to identify drug response using conventional methods may require hours to perform as the response of cells to drugs are usually slow at clinically relevant treatment doses. Furthermore, the response of cells to treatment may not be linear and capturing the complete time dynamics of the response may not be possible if the measurement time is limited. Therefore, such conventional single cell measurements are sensitive to the time of measurement. Even when cells are expected to respond to a particular therapy, the time dynamics of cellular change is difficult to predict. It is particularly difficult for patient samples, where an increased variability is expected compared to cell lines. According to the invention, measuring individual cells of treated and untreated cell populations after cells are incubated for a certain period requires much less time optimization and total instrument time. Comparing the single cell measurements of untreated and treated populations sequentially after this pre-determined dosing interval enables us to measure the time-integral of the cellular response signal independent of the time-dynamics of cellular change.

Figure 2:
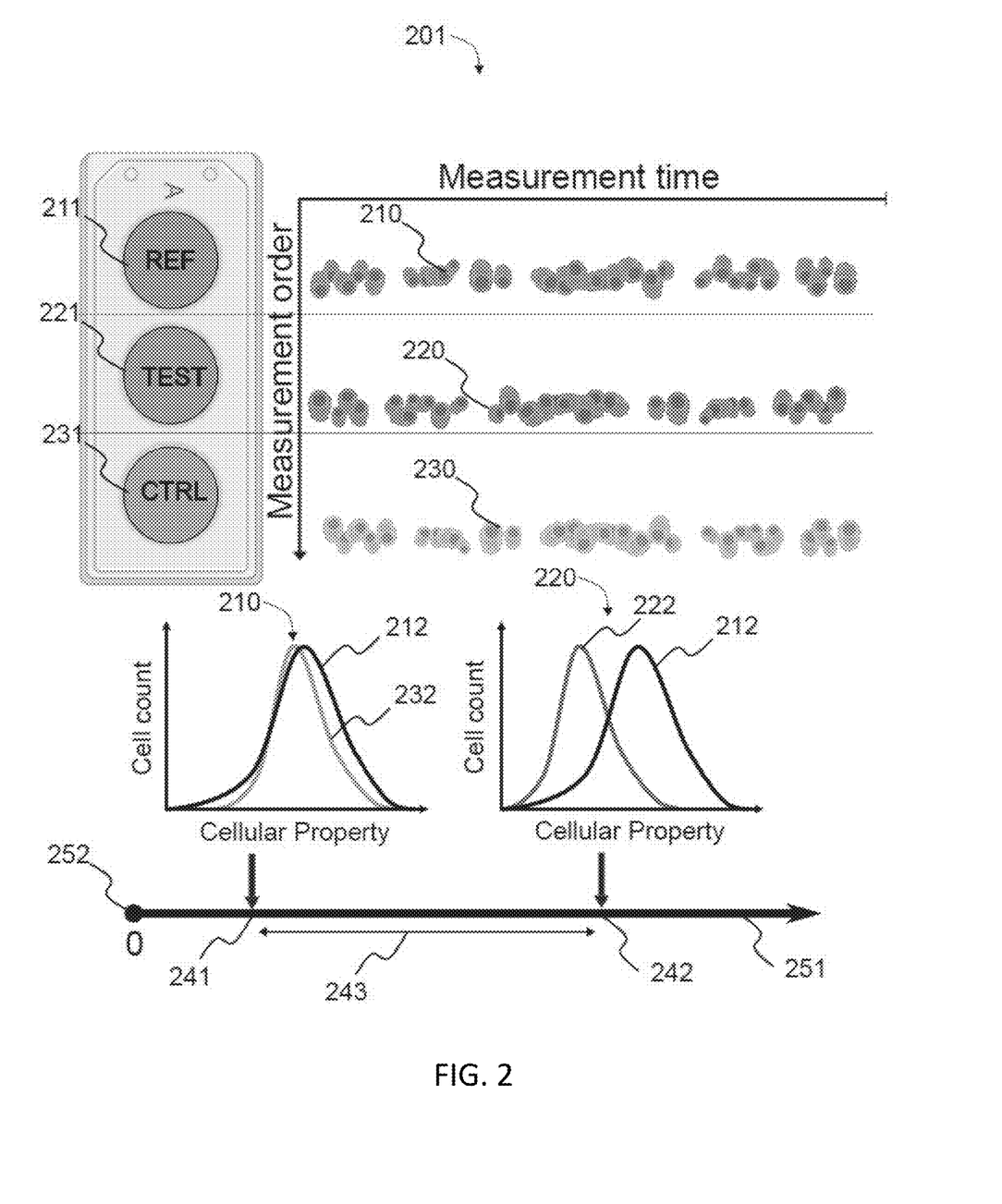
FIG. 2 shows difference in the cellular mass distributions.

The present invention provides an innovative approach that accurately resolves the drug response signal in the presence of cellular time variability. Referring to FIG. 2, cells are prepared under a set of conditions including treatment and no treatment conditions. Then, cells are plated and incubated with treatment 221 and without the treatment 211 and 231 for the dosing period required for the drug. The treated cells are then labeled as "Test" condition 221 and the untreated cells as "Reference" 211 and "Control" 231 conditions. Although FIG. 2 demonstrates the Reference and Control cells as two separate plates, they are identical conditions, and the cells can be drawn from the same plate or vial if necessary.

After the dosing period, cells from these three conditions are measured sequentially in the sensor measuring the cellular property. Cellular property of each cell from each condition is measured individually as a stream of cells. First a portion of cells from the Reference plate 210 is measured by the sensor, which is followed by the cells from Test 220 and Control 230 plates.

The approach of the invention enables measurement of treated cells 220 before and after two sets of untreated cell populations 210 and 230. The difference between the two untreated cell populations (212 vs 232) provides the maximum baseline difference 241 due to possible biological time variability. The relative difference 242 between the treated population 222 and the first set of untreated cells 212 (222 vs 212) compared to the baseline difference 241 provides the net response signal 243 due to the tested treatment modality.

Conventional single cell measurements require a precise calibration of the measurement sensor to ensure accurate, consistent, and comparable measurements across different instruments or sensors. The present invention, on the other hand, eliminates the calibration step so that sensors can be used directly even though their sensitivities are different across instruments or devices. According to the invention, the elimination of calibration is enabled by measuring treated and untreated cells using the same sensor, which ensures that there is no within instrument/chip variability of measurement and using a metric for comparing two populations of single-cell measurements that are measured by the same sensor, wherein the metric is designed to be insensitive to sensor sensitivity and only sensitive to the relative difference between the populations. This is enabled by normalizing the sensor measurements by a statistical property of one of the measured cell populations such as, population mean, median, distribution mode etc. After such normalization, the measurement reported by the sensor is unitless and the outcome is independent of the calibration as any calibration error would alter the population measurements proportionally. In fact, lack of calibration provides the same relative measured signal as a calibrated sensor would provide.

Therefore, to measure the drug response of cells according to the invention, a calibration step is not required. This approach can be extended to any measurement technology that is performed on a target population and the resulting signal is not absolute but relative to a control population.

Once the normalized cellular measurements from untreated and treated populations are collected, the drug response is quantified by calculating the statistical difference between these populations as shown, for example, in FIG. 2. Although standard null hypothesis testing could be used to compare these distributions, a more effective way of quantifying the differences (or similarities) between the measured populations is to utilize a statistical distance metric 251. Although there is a wide range of candidate statistical distance metrics, here we define the properties of an ideal distance metric that would be used to compare two populations of cellular measurements composed of single cell measurements.

According to the invention, an ideal distance metric 251 comparing treated and untreated cells is non-negative. Accordingly, identical populations should result in zero distance 252, indicating no difference between measurements. In addition, the mathematical operation of the distance metric should be symmetric, which ensures identical distance if the two sets of measurements are swapped. The metric should also be sub-additive to ensure correct quantification of response signal when more than one untreated population are measured for the same sample. This ensures an accurate measurement of drug response when there is a non-zero baseline signal 241 due to time variability of cells. In order prevent the impact of an offset during the sensor measurements, the metric should be translational invariant. This ensures that the same distance is measured if all the measurements performed on a sensor has an offset due to a sensor inaccuracy. As examples, statistical distance metrics such as Hellinger distance, Wasserstein distance fit to these ideal properties and are effectively used to quantify the drug response signal.

Figure 3:
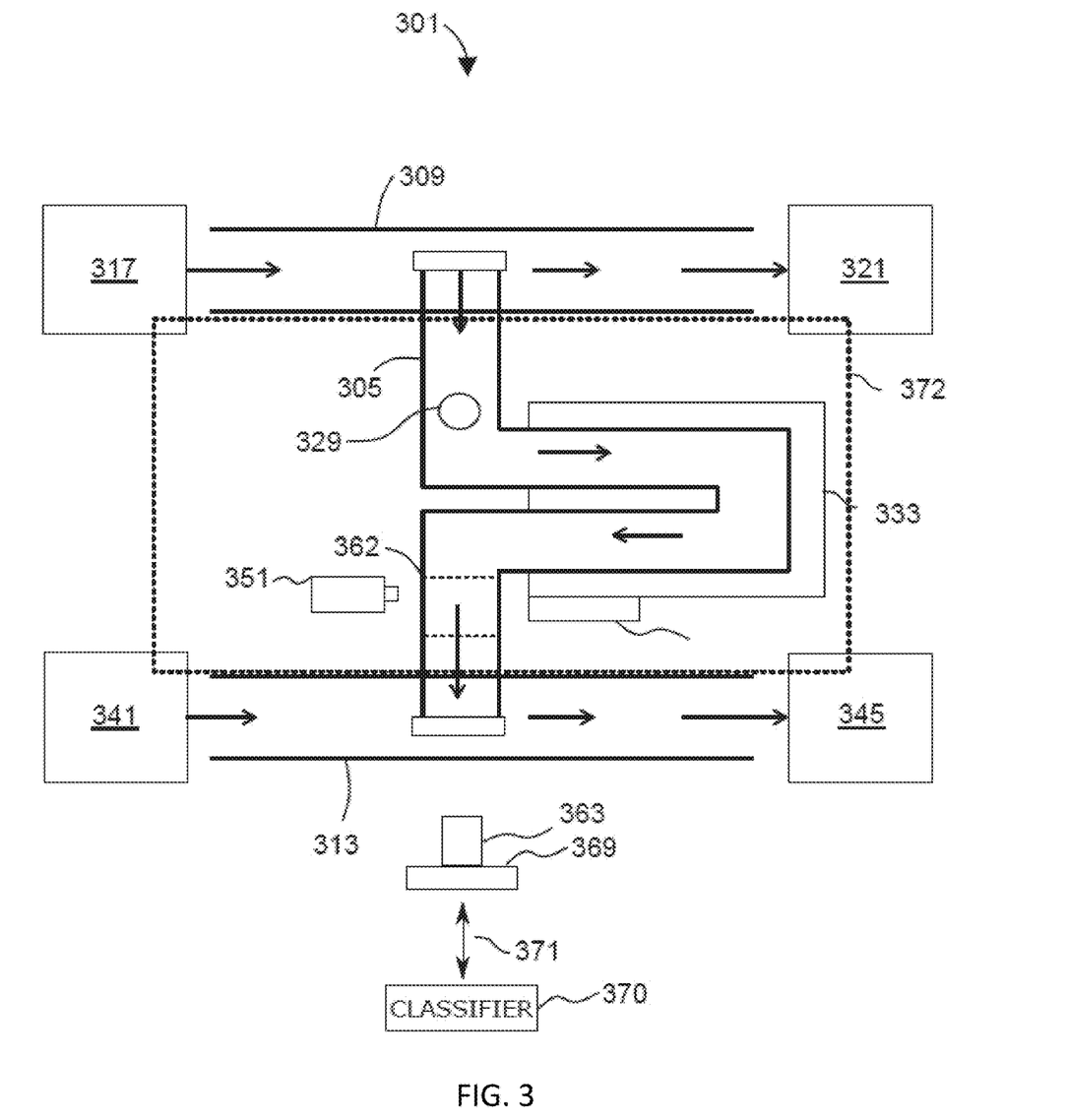
FIG. 3 shows a system of the invention.

Although it is possible to use any single cell sensor according to the invention described, by way of example a measurement using a suspended microchannel resonators (SMR) is provided below. Referring to FIG. 3, an SMR 301 performs precise measurements of single cell mass as cells flow through a microfluidic channel 305 that is embedded into the sensor 333. As shown in FIG. 2, when a stream of cells 210 from a sample 211 is flowed through the sensor, a mass distribution of the sample can be acquired 212.

The changes in cellular mass detected by methods and systems of the invention may reveal, for example, if cells are growing, static or decreasing in mass. Thus, a measured change in the mass of a cell exposed to a treatment modality, e.g., a potential therapeutic, is indicative of a cellular response to the treatment.

While SMR sensors have an exquisite mass resolution enabling mass measurement precisions better than about 50 fg, they are subject to mass sensitivity variation (in units of frequency-per-mass) across SMR sensors within and across chips deteriorating the accuracy of the measurement. Thus, most conventional methods for measuring cellular mass using SMRs require calibration of each sensor before use. The calibration is performed by measuring standard particles with known physical and mechanical properties such as narrow CV polystyrene beads. As described above, the present invention eliminates this requirement and may be employed both within a single instrument utilizing multiple SMR sensors or across instruments without any need for a calibration step.

An exemplary method, system, and device of the invention use an SMR to precisely measure the mass distributions of treated and untreated cells. Changes in mass may reveal a cellular response to a treatment modality. This finds particular application when screening potential treatment modalities, including personalized treatments, for cancer. The mass signal changes in the mass distribution of treated and untreated cancer cells may provide a functional, universal biomarker by which medical professionals (e.g., oncologists) may monitor the efficacy a particular treatment modality has on progression of a cancer and determine how cancer cells respond to therapies. The SMR comprises an exquisitely sensitive scale that measures small changes in mass of a single cell. When cancer cells respond to cancer drugs, the cells may undergo apoptosis and may display a change in mass within hours. The SMR detects even minor mass change over time. Thus, the speed and sensitivity of the SMR allow detection a cancer cell's response to a cancer drug while the cell is still living.

FIG. 3 shows an exemplary SMR device 301 used in the methods, devices, and systems of the invention. The SMR device 301 includes a microchannel 305 that runs through a cantilever 333. The cantilever 333 may be suspended between a sample channel 309 and a waste channel 313. Sample and Waste channels provide a control system to decrease or increase flow resistance and accommodate the control of the flow rate through the microchannel 305.

A cellular eluate 317 which contains treated cells and/or untreated cells (211, 221 or 231) is introduced into the device and the cells flow through the sample channel 309. A portion of the cells flowing through the sample channel 309 enter the microchannel 305 for measurement by the SMR. Cells that are not be measured and/or non-cellular material may flow through the sample channel into a waste reservoir 321. The flow in the sample channel 309 can be adjusted such that all the cells in 309 flow through 305 into the waste channel 313.

Cells 329 to be measured using the SMR (e.g., treated and untreated cells from a sample) are introduced into the suspended microchannel 305 from the sample channel 309. In certain aspects, the flow rate through the suspended microchannel 305 is adjusted by the pressure difference between its inlet and outlet to optimize measurement of cells flowing through the microchannel and/or to cause cells to selectively enter the microchannel from the sample channel. In certain aspects the flow in the sample channel 309 and through the suspended microchannel 305 is controlled by syringe pumps connected to the sample reservoir 317. Since the flow cross section of the suspended microchannel 305 is about 70 times smaller than that of the sample 309 and waste channels 313, the linear flow rate can be much faster in the suspended microchannel than in the sample channel, even though the pressure difference across the suspended microchannel is small. Therefore, at any given time, it is assumed that the SMR device 301 is measuring the cellular eluate, including any cell, that is present at the inlet of the suspended microchannel.

The cells 329 flows through the suspended microchannel 305. The suspended microchannel 305 extends through a cantilever 333. The suspended microchannel 305 may sit between a light source 351 and a photodetector 363 connected to a chip or processor 369 such as a field programmable gate array (FPGA) or a computer. An actuator or resonator 357 may operate on the cantilever 333. The resonator 357 may be a piezo-ceramic actuator seated underneath the cantilever 333 for actuation. After the cells 329 are introduced to the waste channel 313, they may be collected in the waste collection reservoir 345. In certain aspects, cells 329 flow from the sample channel 309 to the inlet of the suspended microchannel 305, through the suspended microchannel 305, and to the outlet of the suspended microchannel 305 toward the waste channel 313. A buffer 341 may flow through the waste channel towards a waste collection reservoir 345.

The SMR device 301 measures the masses of individual cells that flow through the microchannel 305 to provide rapid, high-throughput optimized monitoring of changes to the mass distributions of treated and untreated cells. This data may be used to assess cellular responses to a particular treatment modality. The SMR device 301 comprises an exquisitely sensitive scale such that it may resolve minute differences in cellular masses. The SMR device 301 includes a structure such as a cantilever 333 that contains a fluidic microchannel 305. Cells flow through the structure, which is resonated, and its frequency of resonation is measured. The frequency at which a structure resonates is proportional on its mass. Therefore, as a cell flows in the cantilever 333 through the microchannel 305, the mass of the cantilever is altered changing the frequency at which the cantilever is resonated. By measuring the change of frequency at which the cantilever 333 resonates as a cell flows along the cantilever, the instrument may compute a mass of an individual cell. Thus, in certain preferred methods of the invention, the mass of each cell measured using the SMR is obtained using a single measurement for each cell.

In certain aspects, the mass of individual cells is not explicitly computed using the frequency change of the cantilever 333. The magnitude of the frequency change is used as a proxy for the cell mass. Computation of the mass of a cell from the frequency shift measurement requires the mass sensitivity of the SMR in units of frequency-per-mass. The sensitivity is measured using a calibration step as the non-zero fabrication tolerances of the SMR prevents accurately determining the mass sensitivity of the SMR. Using the method described in this disclosure, it is not required to compute the mass of the cells using the frequency shift as consequently the measured mass of the cells will be normalized with a mass property of the measured population. In certain aspects an approximate mass sensitivity can be utilized to compute an approximate cell mass without impacting the accuracy of the drug response signal.

In certain aspects, the methods of the invention further include measuring the deviation of the resonant frequency at which the cantilever resonates when a particle of cellular or non-cellular material is at a second point along the cantilever to compute structural properties a cell in the fluidic microchannel.

Exemplary suspended microchannel resonator devices 301 include those as described in Cermak, 2016, High-throughput measurement of single-cell growth rates using serial microfluidic mass sensor arrays, *Nat Biotechnol*, 34(10):1052-1059, which is incorporated by reference. Various embodiments of SMR devices 301 and as well as methods of use, include those instruments/devices manufactured by Innovative Micro Technology (Santa Barbara, CA) and as described in U.S. Pat. Nos. 8,418,535 and 9,132,294, which are all incorporated by reference.

The cantilever of the SMR device 301 may be housed in an on-chip vacuum cavity 372, reducing damping and improving frequency (and thus mass) resolution for optimized measurements. As a cell flows through the interior of the cantilever, it transiently changes the resonant frequency of the cantilever in proportion to the buoyant mass of the cell. The SMR device 301 may weigh single mammalian cells with a resolution of 0.05 pg (0.1% of a cell's buoyant mass) or better. Measurements may occur quickly, allowing the SMR to obtain mass distribution(s) for hundreds of living cells a minute.

The SMR device 301 may be fabricated as described in Lee, 2011, Suspended microchannel resonators, Lab Chip 11:645 and/or Burg, 2007, Weighing of biomolecules, *Nature* 446:1066-1069, which are incorporated by reference. Large-channel devices (e.g., useful for peripheral blood mononuclear cells (PBMC) measurements) may have cantilever 333 interior channels of 20 by 20 μm in cross-section, and bypass channels 100 by 35 μm in cross-section. Small-channel devices (useful for a wide variety of cell types) may have cantilever 333 channels 3 by 5 μm in cross-section, and bypass channels 4 by 15 μm in cross-section. The tip of the cantilever 333 in may be aligned so that a single line-shaped laser beam can be used for optical-lever readout.

In certain aspects, before using the SMR for measuring cellular mass, the SMR device may be cleaned with piranha (3:1 sulfuric acid to 50% hydrogen peroxide) and the channel walls may be passivated with polyethylene glycol (PEG) grafted onto poly-L-lysine. In some embodiments, a piezo-ceramic actuator seated underneath the device is used for actuation. The SMR device 301 may include low-noise photodetector, Wheatstone bridge-based amplifier (for piezo-resistor readout), and high-current piezo-ceramic driver. To avoid the effects of optical interference, the instrument may include a low-coherence-length light source (675 nm super-luminescent diode, 7 nm full-width half maximum spectral width) as an optical lever. After the custom photodetector converts the optical signal to a voltage signal, that signal is fed into an FPGA board, in which an FPGA implements parallel second-order phase-locked loop(s) which both demodulates and drives the cantilever. The FPGA may be a Cyclone IV FPGA on a DE2-115 development board operating on a 100 MHz clock with I/O provided via a high-speed AD/DA card operating 14-bit analog-to-digital and digital-to-analog converters at 100 MHz.

To operate the cantilever 333 in the SMR device to measure a cell's mass, the resonator transfer function is first measured by sweeping the driving frequency and recording the amplitude and phase of the SMR's response. Parameters for the phase-locked loop (PLL) is calculated such that the cantilever-PLL feedback loop has a 50 or 100 Hz FM-signal bandwidth. The phase-delay for the PLL may be adjusted to maximize the cantilever vibration amplitude. The FM-signal transfer function may be measured for the cantilever-PLL feedback loop to confirm sufficient measurement bandwidth (in case of errors in setting the parameters). That transfer function relates the measured cantilever-PLL oscillation frequency to the cantilever's time-dependent intrinsic resonant frequency. Frequency data for the cantilever may be collected at 500 Hz, and may be transmitted from the FPGA to a computer. The device may be placed on a copper heat sink/source connected to a heated water bath, maintained at 37 degrees C.

Cells may be loaded into the device from vials pressurized under air or air with 5% CO2 through 0.009 inch innerdiameter fluorinated ethylene propylene (FEP) tubing. The sample may include treated and/or untreated cells from a sample. In certain aspects, treated and untreated cells are introduced into the device together. Alternatively, treated and untreated cells may be introduced into the device separately. The pressurized vials may be seated in a temperature-controlled sample-holder throughout the measurement. FEP tubing allows the device to be flushed with piranha solution for cleaning, as piranha will damage most non-fluorinated plastics. To measure a sample of cells, the SMR may be initially flushed with filtered media.

On large-channel devices, between one and two psi may be applied to the device, yielding flow rates on the order of 0.5 nL/s (the device's calculated fluidic resistance is approximately $3 \times 10^{16}$ Pa/(m3/s). For small-channel devices, 4-5 psi may be applied to the device, yielding flow rates around 0.1 nL/s. In certain aspects, new sample may be periodically flushed into the input bypass channel to prevent particles and cells from settling in the tubing and device. Between experiments, devices may be cleaned with filtered 10% bleach or piranha solution.

Precision frequency detection following identification of particles by a classifier allows the SMR device 301 to measure resonant frequency and mass in single living cells that flow through the device. Precision is the closeness of agreement between independent test results. When determining SMR resonance frequency optically, devices of the invention may use an external laser and photodiode. Alternatively, electronic detection of SMR resonance frequency may be attained by fabricating piezo-resistive sensors using ion implantation into single crystal silicon resonators. The mass resolution achieved with piezo-resistive detection, such as 3.4 femtogram (fg) in a 1 kHz bandwidth, is comparable to what can be achieved by a conventional optical detector designed to weigh micron-sized particles and cells. The use of an SMR device 301 eliminates the need for expensive, delicate optical components and provides new uses for the SMR device 301 in high throughput and field deployable applications. For example, piezo-resistive sensors eliminate the need for external components by measuring deflection through the resistance change of a sensing element integrated onto the cantilever. Microfluidic channels are incorporated inside a cantilever resonator, which significantly reduces viscous damping from fluid and allows buoyant mass to be measured with high resolution.

The methods and systems of the invention extend the robust nature of cellular mass measurements by using a single SMR to resolve difference in the mass distributions of treated and untreated cells. It has been shown that the change in mass accumulation rate (MAR) of cancer cells when treated with particular drugs can predict patients' therapeutic response to these therapies. Therefore, such an approach could be used to guide treatment strategies of cancer patients. However, measuring single cell MAR has unique difficulties and shortcomings such as the extended time required to test a drug condition (>2 hours), inability of establishing a control measurement in the same instrument, sensitivity of the method to small calibration error, and the difficulty of establishing optimal dosing time that maximizes the MAR signal across drugs, cancer types and/or biopsy samples.

The present invention alleviates these drawbacks of prior methods for single cell MAR. The present invention thus provides an alternative approach to resolve the response of cells, such as cancer cells, to a particular treatment modality based on single cell mass measurements, while addressing the shortcomings of single cell MAR approach. In contrast to MAR measurements, which require multiple mass measurements of each individual cell (>10 times), the preferred methods of the present invention measure each cell in the treated test and untreated control portions only once. This approach enables a flow of a serial stream of cells (untreated cells and treated cells) through the same SMR, while measuring the mass of each individual cell in the stream.

Measuring each cell only one time with the SMR enables the methods of the invention measure cells as they rapidly flow through an SMR device. This minimizes the measurement duration down to minutes instead of hours therefore enables testing of numerous treatment modalities in a relatively short timeframe.

Further, immediately after the biopsy, extracted cells, such as tumor cells, may start to lose their viability ex vivo and naturally start to present time variability. The rate of this biological time variability depends highly on the conditions the cells are kept in, as well as other factors, e.g., cell or tumor type, particularities of a patient, and the like. Given enough time, cellular time variability may manifest itself initially as reduction in cell mass. Therefore, certain methods of the invention include monitoring of baseline time variability in the mass of untreated cells to accurately identify mass change signals in the mass distributions attributed to a treatment modality. In certain aspects, the fast flow rates utilized in the methods of the invention enable measurement of treated cells before and after two sets of untreated cell populations. The difference between the two untreated cell populations may provide the maximum baseline mass difference due to a possible biological time variability. The relative difference between the treated cells and the first set of untreated cells versus this baseline mass difference provides the net mass response signal due to the drug tested.

Moreover, the methods and systems of the invention do not require a mass calibration step of the SMR sensor. Thus, the presently disclosed methods can be used on various SMR sensors directly even though their mass sensitivities are relatively different across instruments or chips. The invention eliminates the calibration requirement because only a single SMR is used, which ensures that there is no within instrument/chip variability. Moreover, the metric (mass distributions) used for comparing two populations of single-cell masses that were measured by the same SMR sensor is insensitive to the mass sensitivity of the SMR sensor as it is a relative measurement between the mass distributions of different populations of cells.

FIG. 2 shows exemplary results and analysis using the methods of the invention. The two panels 210 and 220 show normalized mass distributions (normalized to population mean) measured using the same SMR between two control cell populations treated with DMSO (Reference and Control conditions) and between a control cell population and that subjected to a treatment modality, in this case, a drug. Differences between the control cell and treatment modality distributions are indicative of a cellular response to the drug. These differences may include, for example, the ranges of the distributions. Differences indicative of a cellular response may also include differences between the shapes of the distributions, e.g., the magnitudes and widths of peaks in the distributions. As shown in FIG. 2, metrics such as the Hellinger distance, Wasserstein distance, etc. may be used to compare the distributions of the control and treatment conditions and quantify these differences across the populations. In this example, the distance between the two control conditions 212 and 232 is measured as 241 and the distance between the treatment modality 222 and the control 212 conditions is measured as 242. The difference 243 between these distances is the net response signal of the cells to the treatment modality. As these distributions 212, 222, 232 are unitless, the present invention can provide measures of cellular response to a treatment modality without a calibration step. Further, this approach can be extended to any measurement technology that is performed on a target population and the resulting signal is not absolute but relative to a control population.

Further, under certain circumstances the present invention may provide measurements equivalent to those obtained using single-cell MAR. Single-cell MAR is the time derivative of cell mass. Therefore, the signal measured is sensitive to the time of measurement. Even when cells are expected to respond to a particular therapy, the time dynamics of cell mass change is difficult to predict. It is particularly difficult for patient samples, where an increased variability is expected compared to cancer cell lines. Comparing the mass of cells in treated and untreated populations after a predetermined dosing interval enables methods of the present invention to measure the time-integral of the MAR signal, independent of the time-dynamics of mass change. The presently disclosed methods are particularly effective if the dosing interval is long enough to capture most of the mass change in the treated cells and when the untreated control cells do not considerably alter their mass due to biological time variability. Nevertheless, the present invention includes methods that monitor the natural time variability of cells, for example, by using the second set of untreated control cells measured after the treated cells.

In certain aspects, the SMR device used in the methods and systems of the invention with a classifier the directs the flow of cells and/or non-cellular material through the device. As shown in FIG. 3, the device may use a classifier 370 coupled to, for example, a brightfield sensor 363, to provide additional characterization of cells the flow through the device.

FIG. 3 shows an exemplary measurement device that includes a single SMR and uses a classifier to control the flow of cells and/or non-cellular material. The measurement device includes a sample channel 309 and a secondary measurement channel 305. A sample that includes cells (e.g., treated and/or untreated cells) and, possibly, non-cellular material is introduced to the sample channel and flows through the measurement channel 305 to a sensing region 362 comprising a sensor 363. The sensor may operate over the sensing region 362 and collects data from the cellular and/or non-cellular material that flows through the sensing region 362. The sensor then provides the data to be processed in a processor 369. The processed data 371 is sent to a classifier 370. Depending on its configuration, the classifier may use the data from the sensor 363 to identify, for example, cells, target cells, treated cells, untreated cells, and/or non-cellular material. The measurement device controls the flow of cellular and/or non-cellular material through the measurement channel 305. The measurement device may comprise a control system for receiving the identification from the classifier 370 and control the flow of cells through the sample 309 and measurement 305 channels. The SMR 333 is disposed in the measurement channel where it measures the masses of cells that flow through the device.

In certain aspects, cells are labeled with a label that is detected by the sensor 363 in the sensor region 362. For example, a label may include an optically detectable label and the sensor includes a fluorescence detection sensor to detect the label. The classifier 370 may identify the label form the sensor and identify the cell based on the presence and/or absence of a label. For example, in certain methods, treated cell are labeled to distinguish them from untreated cells. Consequently, treated, and untreated cells may be concurrently introduced in the SMR device from the same vial or plate, and the classifier is able to identify cells as treated or untreated. Thus, the SMR may measure the mass of treated and untreated cells at the same time, as the label may be used to correlate a cell mass measurement with a treated or untreated cell. Similarly, treated and untreated cells may be identified such that the device selectively flows treated or untreated cells through the SMR for measurement. Alternatively or additionally, labels may be used to identify target cells (e.g., treated and untreated cancer cells) to distinguish them from non-target cells (e.g., non-cancer cells).

In certain aspects, the sensor 363 is an imaging sensor that includes an array of sensor elements. Sensor elements may include photoelectric sensor elements. Imaging sensors collect data about light or diffraction patterns incident upon sensor elements from cells and/or non-cellular materials in the sensing region. Upon receiving a signal to capture an image from the sensing region, incoming light from cells flowing through the sensor region reach an array of sensor elements of the imaging sensor. Each sensor element may collect and store photons from light as an electrical signal. By having an array of sensor elements configured to capture cells flowing through the device, the imaging sensor may record a present state of the sensing region for the classifier. When sensing color images, the imaging sensor may have a color filter array (CFA) that limits each sensor element to only collect incoming light for a particular color, for example each sensor element may capture light that corresponds to only one primary color.

After light exposure upon the array of sensor elements, the electrical signal from the individual sensor elements may then be used to reproduce the image of the sensing region by configuring the color and brightness of matching pixels to the electrical signals. A computer may be provided to match pixels to recreate the image. In some instances, for every sensor element there may be a corresponding pixel within the recreated image that reflects the charge and color received at the sensor element from the sensing region. The classifier may identify, for example, cells, labels, and/or non-cellular material based on the recreated image of the sensing region. The classifier may also identify material directly from the electrical signals provided by the sensor.

The imaging sensor may include a lens and/or may comprise a camera such as a digital camera. The imaging sensor may be a charge-coupled device (CCD) or may be a complementary metal-oxide-semiconductor (CMOS) sensor. CCD and CMOS sensors can be arranged in a two-dimensional array to capture two-dimensional image signals. Sensor size and/or the number of sensor elements may be used to control the spatial resolution of the image captured. The resolution may be pixel resolution. Increasing the density of sensor elements increases spatial resolution. Increasing the size of sensors increases the amount of light incident on each sensor. Imaging detail may be limited by optics due to lens blurs, lens aberration effects, aperture diffractions, and optical blurring due to motion.

The imaging sensor may advantageously be a lens-free imaging sensor, for example an imaging sensor that does not comprise correction lenses or components. The lens-free imaging may be on chip imaging using a digital optoelectric sensor array, such as a CCD or CMOS chip. Imaging chips and optical components provide the advantage when used with the classifier of capturing very high-resolution images. The chip may directly sample light transmitted through a source without the use of any imaging lenses between the source and the sensor planes. Lens-free imaging sensors can advantageously comprise more compact, lightweight, and simpler hardware than lens-based sensors. Lens-free imaging sensors are described in Greenbaum, 2012, Imaging without lenses: achievements and remaining challenges of wide-field on-chip microscopy, Nat Methods, 9(9):889-895, incorporated by reference.

The classifier may identify treated and untreated cells based on an image of the sensing region. The image may have a pixel resolution. The classifier may also identify cells and/or non-cellular materials directly from the electrical signals provided by the sensor elements.

Figure 4:
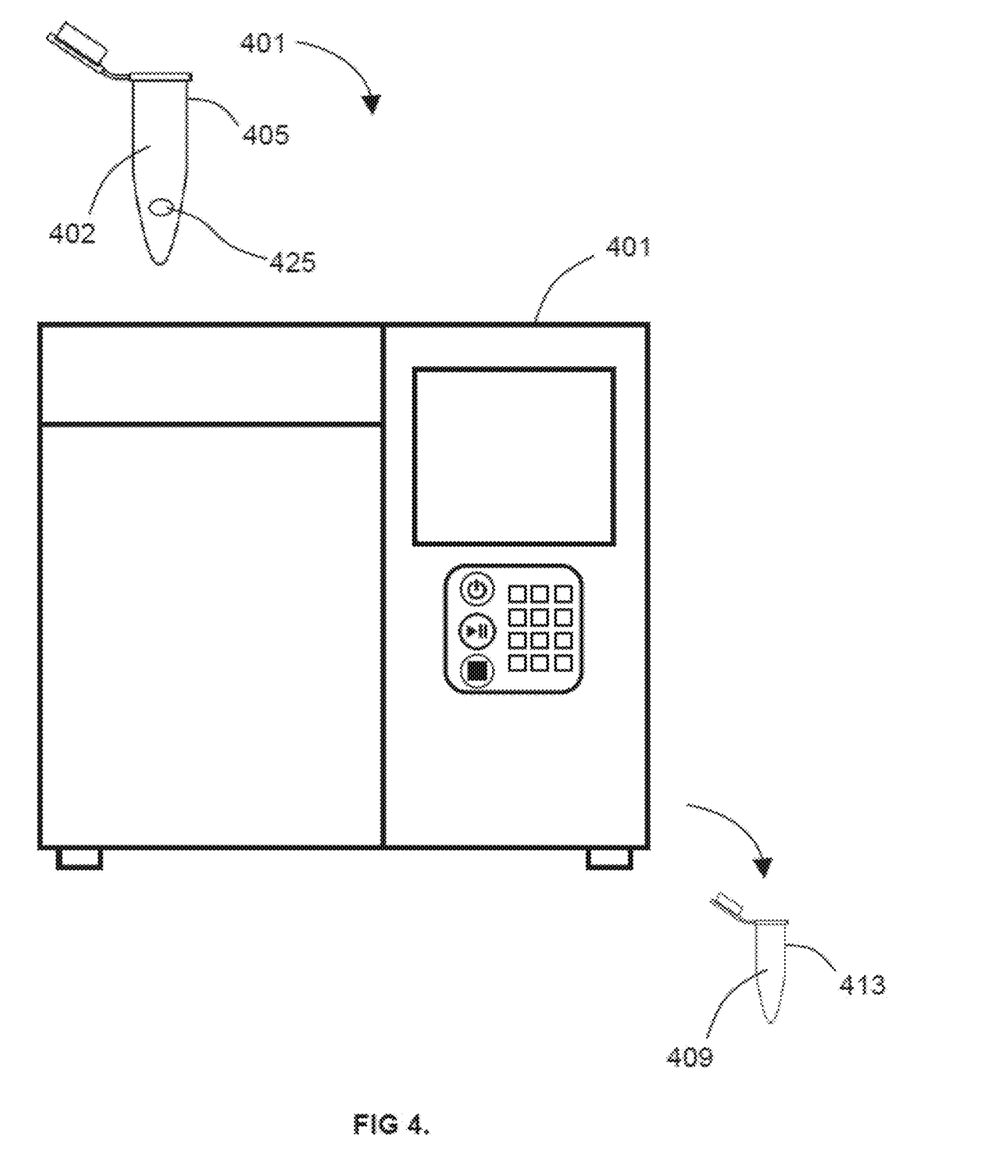
FIG. 4 shows device of the invention.

FIG. 4 shows an SMR instrument capable used in the methods of the invention. A sample 401 may include treated and/or untreated cells, which may be, for example, cancer or immune cells. Samples may be collected and stored in their own container 405, such as a tube or flask such as the 1.5 mL micro-centrifuge tube sold under the trademark EPPENDORF FLEX-TUBES by Eppendorf, Inc. (Enfield, CT). Live cells from the sample 401 are introduced into the SMR instrument. After measurement using the SMR, and upon passing through the instrument, single cells may remain viable and can be isolated downstream from the instrument and are available to undergo subsequent assays. As shown, a sample 409 of the one or more live cells having undergone the first assay (i.e., passing through the instrument) are collected in a suitable container 413 and are then available to undergo a second assay.

Mass change signals may reveal cellular responses indicative of the efficacy of a particular treatment modality. In certain aspects, cancer cells may be obtained from a patient and a portion of them treated with a treatment modality. Treated and untreated cells are introduced into the measurement device of the present invention. Cells may be from a biological sample obtained from a patient by any suitable means. Examples of obtaining the sample include fine needle aspiration, blood draw, and biopsy.

Fine needle aspiration and bone marrow biopsy provide a solid biological sample from the patient, providing the ability to sample from pleural effusions and ascites. Accordingly, the sample does not need to be in liquid form. Solid biological samples, for example from fine needle aspiration, may preferably be disaggregated and/or added to a buffer prior to introduction to the instrument. Accordingly, optimized cellular measurements may be obtained from cells from a tissue sample obtained from a solid tumor and the tumor can be from one selected from the group consisting of a bone, bladder, brain, breast, colon, esophagus, gastrointestinal tract, urinary tract, kidney, liver, lung, nervous system, ovary, pancreas, prostate, retina, skin, stomach, testicles, and uterus of a subject. The methods may be used to obtain tumors or cancers of any suitable type. Methods may include accessing a tumor in a patient via fine needle aspirate to take a biological sample comprising cancer cells, disaggregating the biological sample to isolate at least one living cell. The solid biological sample may then be suspended in a media and introduced to the measurement instrument. Non-limiting examples of media include saline, nutrient broth, and agar medium. Examples of biopsies that may provide cells for optimized cellular measurement using systems and methods described herein can include, needle biopsy, bone biopsy, bone marrow biopsy, liver biopsy, kidney biopsy, aspiration biopsy, prostate biopsy, skin biopsy, or surgical biopsy.

A tissue sample may include a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues.

Liquid material derived from, for example, a human or other mammal such as body fluids may also be utilized. Such body fluids include, but are not limited to, mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS. A sample also may be media containing cells or biological material. A sample may also be a blood clot, for example, a blood clot that has been obtained from whole blood after the serum has been removed. In certain embodiments, the sample is blood, saliva, or semen collected from the subject.

Any suitable sample may be obtained for optimized cellular measurements by the methods and systems of the invention. For example, the sample may include immune cells or cancer cells. The sample may include tissue of any type including healthy tissue or bodily fluid of any type. In some embodiments, the tissue sample is obtained from a pleural effusion in a subject. A pleural effusion is excess fluid that accumulates in the pleural cavity, the fluid-filled space that surrounds the lungs. This excess fluid can impair breathing by limiting the expansion of the lungs. Various kinds of pleural effusion, depending on the nature of the fluid and what caused its entry into the pleural space, may be sampled. A pneumothorax is the accumulation of air in the pleural space, and is commonly called a "collapsed lung". In certain embodiments, the tissue sample is obtained from ascetic fluid in a subject. Ascites is the accumulation of fluid (usually serous fluid which is a pale yellow and clear fluid) that accumulates in the abdominal cavity. The abdominal cavity is located below the chest cavity, separated from it by the diaphragm. The accumulated fluid can have many sources such as liver disease, cancers, congestive heart failure, or kidney failure.

The biological sample may include a fine needle aspirate or a biopsy from a tissue known to be, or suspected of being, cancerous. The sample may include a bodily fluid from a patient either known to include, or suspected of including, cancer cells or cancer-related cells (i.e., immune cells).

Accordingly, the cancer cell may be from a patient having or suspected of having a cancer. Types of cancer are characterized by the cells from which they originate. Cancer types include carcinomas such as breast, prostate, lung, pancreatic, and colon cancers that arise from epithelial cells. Sarcomas are derived from connective tissue (e.g., bone, cartilage, fat, or nerve cells). Lymphoma and leukemia arise from hematopoietic cells and are found in the lymph nodes and blood of afflicted patients. Cancer of plasma cells (myeloma) is another cancer found in blood. Germ cell cancers derived from pluripotent cells and blastomas from precursor cells or embryonic tissue are other types of cancer. Cancers may be categorized by those detectable in body fluids, for example, lymphoma, leukemia, or multiple myeloma, as well as those detectable in solid tumors, for example carcinomas or sarcomas. Optimized measurements of the present systems and methods may be used to measure cancers detectable in body fluids or cancers detectable in solid tumors. Accordingly, the cancer may be a leukemia, a lymphoma, a myeloma, a melanoma, a carcinoma, or a sarcoma. In certain embodiments, the cancer involves a solid tumor of, for example, the esophagus, kidneys, uterus, ovaries, thyroid, breast, liver, gallbladder, stomach, pancreas, or colon.

Optimized cellular measurement of properties, such mass changes measured in cells, can reveal, for example, if the cells are growing, stationary, or atrophying. Those features of cellular life may be hallmarks of health, cancer, or drug response, and thus methods and devices of the disclosure are valuable tools for precision medicine. Precision Medicine refers to the tailoring of medical treatment to individual characteristics of a patient and the ability to classify individuals into subpopulations that differ in their susceptibility to a particular disease or treatment. Precision medicine often involves genomic or molecular analysis of an individual patient's disease at the molecular level and the selection of targeted treatments to address that individual patient's disease process. In theory, therapeutic interventions are concentrated on those who will benefit, sparing expense and side effects for those who will not. Historically, next-generation sequencing (NGS) technologies make up the core of precision medicine. Clinicians use NGS technologies to screen for cancer-associated mutations or to study gene expression levels. Now, when coupled with existing approaches based on next-generation sequencing, functional measurements according to the invention provide for multi-dimensional precision medicine with benefits in disease areas such as oncology.

Methods and devices of the invention may be used to identify the effect of a treatment modality on malignant cancer cells in a blood or tissue sample from a patient. These tools may provide an ex vivo test of drug response, useful for therapeutic selection. For example, optimized measurement of MAR in cells provides a measure of cancer in a patient. After treatment of a patient, optimized cellular measurements may be used to monitor recurrence, remission, or relapse. Thus, the invention provides for the improvement of patient care, greater chances of successful cancer treatment, and increased patient life spans. Cancer cells may be obtained from a patient treated for cancer, and the measurement of MAR by the methods and devices of the invention may be used to monitor the effectiveness of the cancer treatment.

Methods and devices of the disclosure are useful for precisely and rapidly measuring growth rates of living individual cells using a small amount of a sample. Only a small amount of a sample may be used to observe and measure a single cell, as opposed to observing a population of cells in traditional methods. Therefore, a small amount of cells can be obtained directly from a subject, suspended in media, and then introduced to a measurement instrument without the need to add additional time-consuming steps, such as culturing the cells. In the invention, the cells from the biological sample are separated when flowing through a microfluidic channel of the measurement instrument and the growth rate of individual cells is measured.

A small sample size may be required as compared to sample sizes necessary in other measurement methods. For example, the sample may comprise about 500 or fewer cells. A small amount of cells may be used because of the precision of the methods of measurement. Therefore, the optimized measurement of the present invention may be advantageous when limited tissue samples are available for testing and measurement. For example, a tissue sample may comprise about 10,000 cells. Such a tissue sample does not have enough cells present in the sample for traditional measurement methods, such as optics measurement methods. Therefore, because 500 or fewer cells may be used, if a sample of about 10,000 cells is provided 20 different test conditions may be tested. For example, 500 cells may be dosed with a first drug to determine the effects of the drug on mass accumulation rate of the cells. Therefore, as many as 20 different drugs may be tested with a sample containing 10,000 cells.

Figure 5:
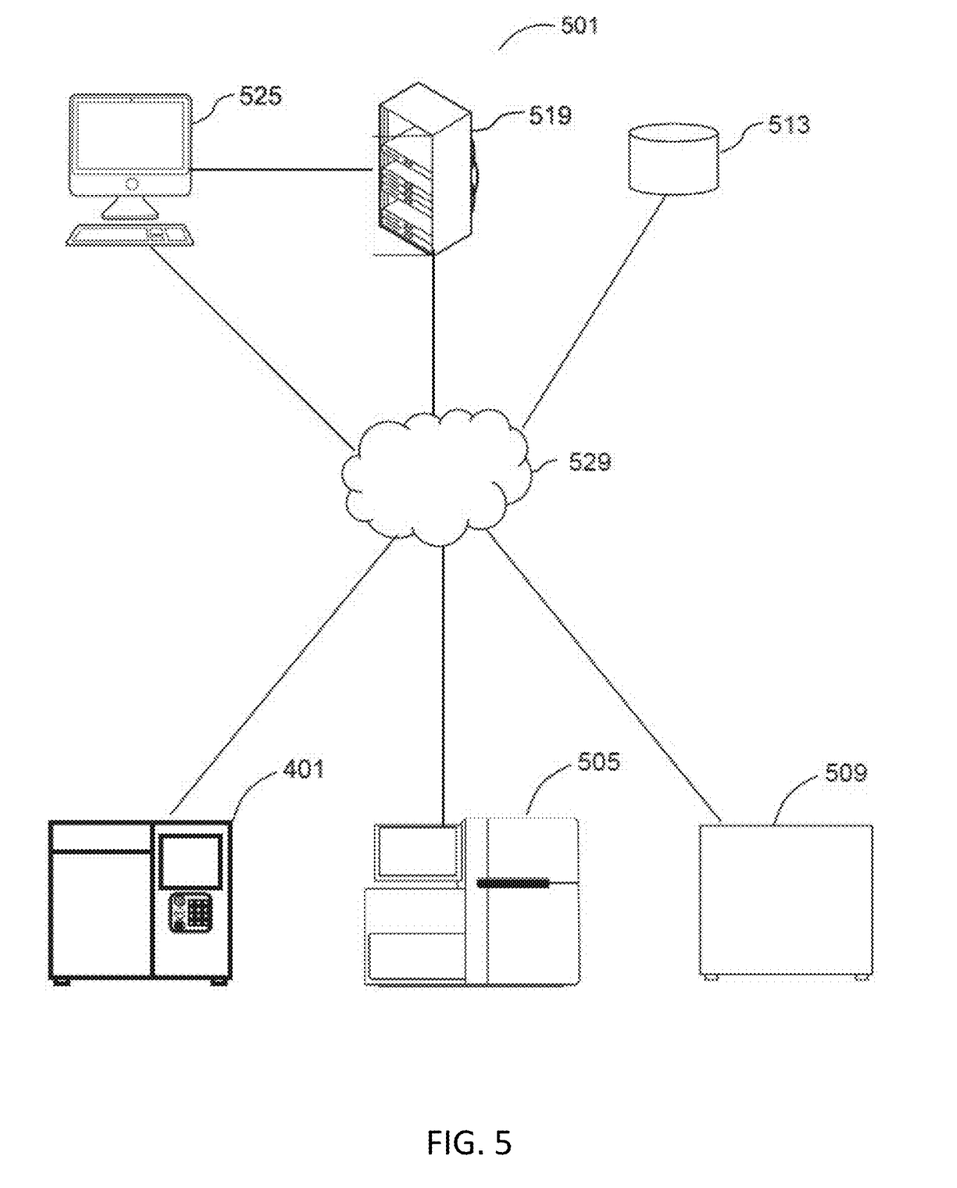
FIG. 5 shows a system of the invention.

FIG. 5 shows an exemplary system 501 useful for performing methods of the disclosure. Preferably, the system provides an SMR instrument 401 capable of making optimized cell measurements and at least one computer 525. The system 501 also preferably includes at least one server 519. The instrument includes a single SMR device 301 used to measure the mass distributions of cells.

The instrument may include a classifier 555. The classifier may operate in real-time, and the identification of cells and/or non-cellular material and may be used to control flow through the instrument 401. Either or both of the computer 525 and the server 519 may include and provide the classifier 555. The system 501 may optionally also include any one or more of a storage 513, a sequencing instrument 505, and any additional analysis instruments 509 for performing additional assays on the one or more cells downstream of the initial assay performed by instrument 401. Any of those elements may interoperate via a network 529. Any one of the instruments may include its own built-in or connected computer which may connect to the network and/or the server. The instrument 401, for example, may have its own computer or server which provides the classifier. The computer 525 may include one or more processors and memory as well as an input/output mechanism. Where methods of the invention employ a client/server architecture, steps of methods of the invention may be performed using the server, which includes one or more of processors and memory, capable of obtaining data, instructions, etc., or providing results via an interface module or providing results as a file. The server 519 may be provided by a single or multiple computer devices, such as the rack-mounted computers sold under the trademark BLADE by Hitachi. The server 519 may be provided as a set of servers located on or off-site or both. The server 519 may be owned or provided as a service. The server 519 or the storage 513 may be provided wholly or in-part as a cloud-based resources such as Amazon Web Services or Google. The inclusion of cloud resources may be beneficial as the available hardware scales up and down immediately with demand. The actual processors—the specific silicon chips—performing a computation task can change arbitrarily as information processing scales up or down. In an embodiment, the server 519 includes one or a plurality of local units working in conjunction with a cloud resource (where local means not-cloud and includes or off-site). The server 519 may be engaged over the network 529 by the computer 525.

In the system 501, each computer preferably includes at least one processor coupled to a memory and at least one input/output (I/O) mechanism. A processor will generally include a chip, such as a single core or multi-core chip, to provide a central processing unit (CPU). A processor may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Generally, each computer includes a non-transitory memory such as a solid-state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro-SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

The system 601 or components of system 601 may be used to perform methods described herein. Instructions for any method step may be stored in memory and a processor may execute those instructions, including use and training of a classifier for identifying cellular and/or non-cellular material.

The system 501 thus includes at least one computer (and optionally one or more instruments) operable to obtain one or more live cells isolated from a sample of a patient, wherein the one or more live cells comprise at least one of a cancer cell and a cancer-related immune cell. The system 501 is further operable to perform a first assay on cellular and/or non-cellular material, wherein the first assay comprises making an optimized cellular measurement by the methods and systems of the invention. The system 501 is optionally further operable to perform a second assay on the one or more live cells having undergone the first assay. The system 501 is further operable to analyze data from the second assay and the optimized measurement from the first assay to determine at least a stage or progression of the cancer. Using the computer 501, the system is operable to provide a report comprising any suitable patient information including identity along with information related to the cancer evaluation, including, but not limited to, specific data associated with the first and second assays, a determination of a stage or progression of cancer, and personalized treatment tailored to an individual patient's cancer.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A method for assessing cellular response to a treatment, the method comprising the steps of:
    exposing a first portion of a biological sample comprising live cells to a treatment;
    sequentially measuring a property of an untreated second portion, the first portion, and an untreated third portion of the sample;
    normalizing the measurements of the first, second, and third portions with respect to the property;

establishing a baseline measurement as a difference between measured properties of the untreated second and third portions of the sample;

comparing the measured property of the first portion to the baseline; wherein a difference between the measured property of the first portion and the baseline is indicative of a cellular response to the treatment.

2. The method of claim 1, wherein the measuring steps comprise measuring a change in mass of the live cells.

3. The method of claim 2, wherein the system further uses an imaging sensor to image the live cells.

4. The method of claim 1, wherein the sample comprises cancer cells.

5. The method of claim 1, wherein the treatment is a putative therapeutic.

6. The method of claim 1, wherein the property is selected from the group consisting of mass, volume, diameter, impedance, capacitance, resistance, optical properties, density, stiffness, surface friction, deformation, cell-cycle state, viability, differentiation state, activation state, and fluorescence.

7. The method of claim 1, wherein the said measurement is conducted on single cells.

8. The method of claim 1, wherein the property of the untreated portions is a mean or median obtained in said measuring step.

9. The method of claim 1, wherein the property of the untreated portions is a mode obtained in said measuring step.

10. The method of claim 1, wherein the comparing step comprises a metric selected from a Hellinger distance and a Wasserstein distance.

11. The method of claim 1, wherein the measuring steps are conducted on a suspended microchannel resonator.

12. The method of claim 11, wherein the suspended microchannel resonator comprises a sample channel, a measurement channel, and an additional sensor operating over the measurement channel.

13. The method of claim 12, wherein the additional sensor is an imaging sensor.

14. The method of claim 12, wherein the additional sensor is a fluorescence detector.

15. The method of claim 11, wherein the method further comprises labeling the treated and/or untreated portions with a detectable label.

16. The method of claim 15 wherein the treated and untreated portions are introduced into the suspended microchannel resonator together.

17. The method of claim 1, wherein the method does not include a calibrating step.

18. The method of claim 1, wherein the step of sequentially measuring a property is performed using at least one suspended microchannel resonator that includes a channel extending through a cantilever positioned between a light source and a photodetector.

19. The method of claim 18, wherein the photodetector is connected to a computer.

20. The method of claim 19, wherein the at least one suspended microchannel resonator further includes a sample channel and a waste channel.

* * * * *